(12) United States Patent
Donlon et al.

(10) Patent No.: US 6,492,654 B1
(45) Date of Patent: Dec. 10, 2002

(54) SCANNING SYSTEM WITH FLEXIBLE DRIVE ASSEMBLY

(75) Inventors: Edward P. Donlon, San Jose, CA (US);
Joseph R. Rimsa, Alameda, CA (US);
Louis Hlousek, Reno, NV (US)

(73) Assignee: Alara, Inc., Hayward, CA (US)

( * ) Notice: Subject to any disclaimer, the term of this patent is extended or adjusted under 35 U.S.C. 154(b) by 0 days.

(21) Appl. No.: 09/782,923

(22) Filed: Feb. 13, 2001

Related U.S. Application Data

(63) Continuation of application No. 09/172,808, filed on Oct. 14, 1998, now Pat. No. 6,198,111.

(51) Int. Cl.[7] .............................................. G01N 23/04
(52) U.S. Cl. ...................................... 250/584; 250/591
(58) Field of Search ................................ 250/584, 591, 250/581, 585, 586

(56) References Cited

U.S. PATENT DOCUMENTS

| | | | |
|---|---|---|---|
| 2,587,145 A | 2/1952 | Grib ............................ | 346/113 |
| 3,553,359 A | 1/1971 | Dixon et al. ................. | 358/498 |
| 5,144,135 A | 9/1992 | Hendrix et al. .............. | 250/580 |
| 5,249,858 A | 10/1993 | Nusser ...................... | 321/319.6 |
| 5,276,464 A | 1/1994 | Kerr et al. ................... | 346/134 |
| 5,590,167 A | 12/1996 | Arai ............................ | 378/38 |
| 5,635,728 A | 6/1997 | Cantu et al. ................. | 250/584 |
| 6,198,111 B1 * | 3/2001 | Donlon et al. .............. | 250/584 |

FOREIGN PATENT DOCUMENTS

| WO | WO 92/15798 | 9/1992 | ............. F16D/3/79 |
|---|---|---|---|

\* cited by examiner

*Primary Examiner*—Constantine Hannaher
*Assistant Examiner*—Albert Gagliardi
(74) *Attorney, Agent, or Firm*—U.P. Peter Eng; Wilson Sonsini Goodrich & Rosati

(57) ABSTRACT

A system is provided for scanning an object, the system comprising: a drive shaft having a proximal portion and a longitudinal axis; a motor including a motor shaft having a rotational axis, the motor serving to rotate the motor shaft about the rotational axis; a flexible joint coupling the drive shaft to the motor shaft by the proximal portion of the drive shaft, the flexible joint having a range of motion which allows the longitudinal axis of the drive shaft to move relative to the rotational axis of the motor shaft; and an object attached to the drive shaft which is movable along the longitudinal axis of the drive shaft in response to the drive shaft being rotated by the motor. This system may be used in a drum scanner system and may be used to read storage layer radiation screens.

3 Claims, 9 Drawing Sheets

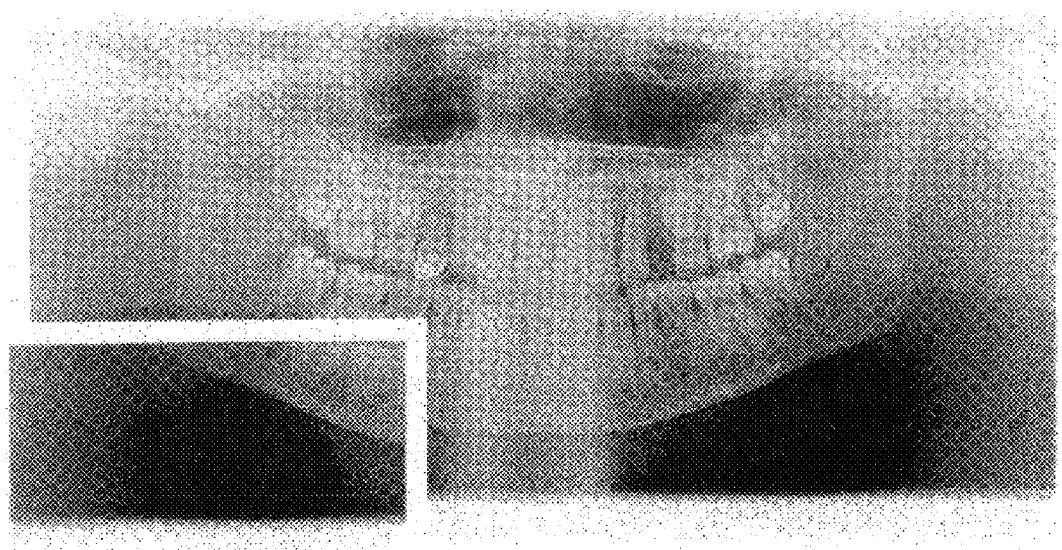
Fig. 6A
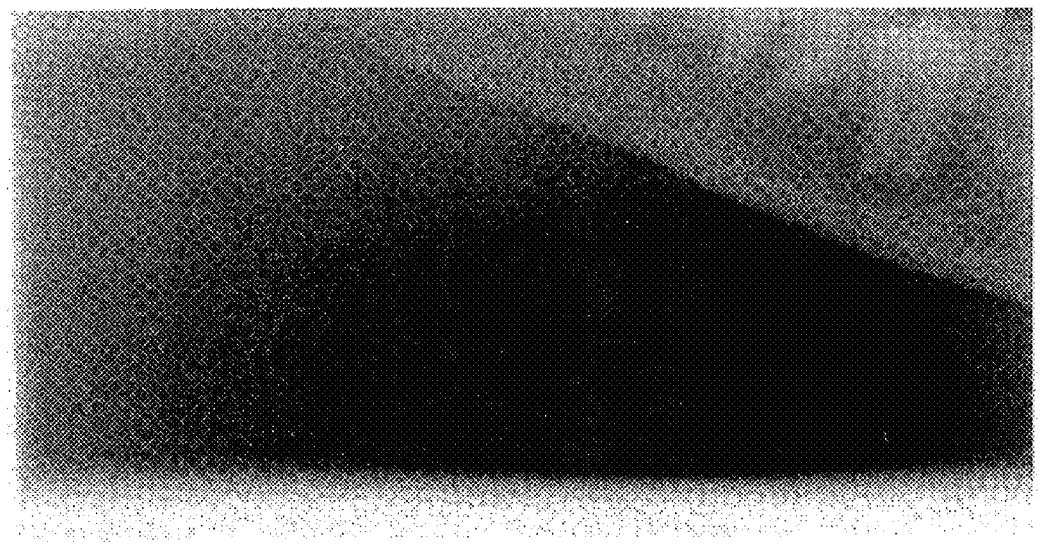

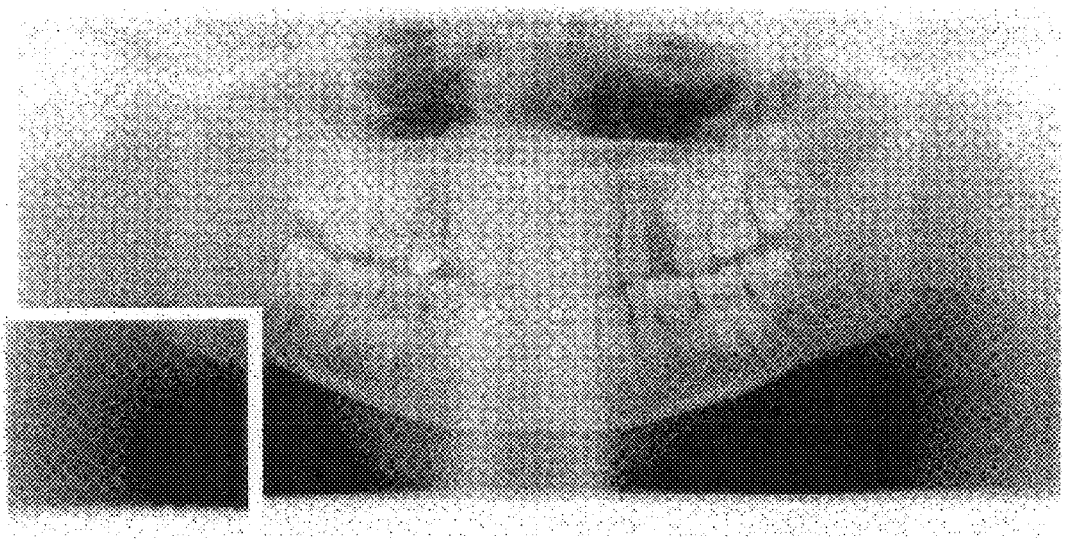
Fig. 6B
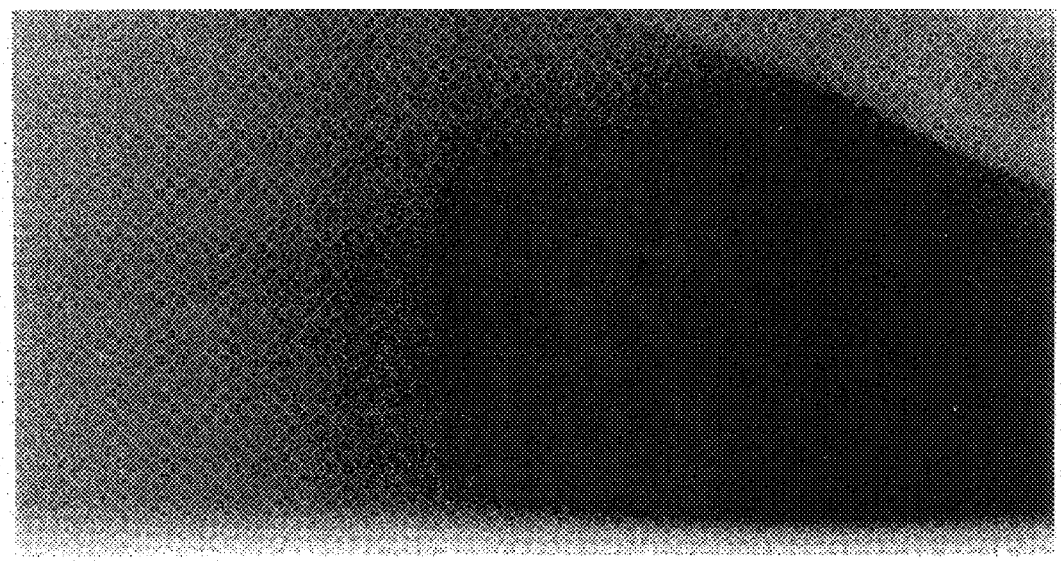

SCANNING SYSTEM WITH FLEXIBLE DRIVE ASSEMBLY

This application is a continuation of U.S. application Ser. No. 09/172,808, filed Oct. 14, 1998, now U.S. Pat. No. 6,198,111, which is incorporated herein by reference in its entirety.

BACKGROUND OF THE INVENTION

1. Field of the Invention

The present invention relates to a drive assembly system. More specifically, the present invention relates to a drive assembly which provides a scanning system with improved images.

2. Description of the Related Art

Radiation images, such as those in radiography and tomography, can be stored in conventional x-ray films or in storage layer radiation screens. Storage layer radiation screens have significant advantages of requiring lower levels of x-ray radiation to produce radiation images, and are reusable after an erasing and sterilization process. A typical storage layer radiation screen can be used for recording images of an object, such as a part of human body, exposed to radiation. The screen is then scanned with stimulating rays, such as a laser beam which causes the phosphors in the screen to emit light in proportion to the amount of radiation absorbed by the portion of the screen being scanned. The light emitted from the screen is then detected and converted into an electrical signal. The electrical signal is then used to reproduce the latent radiation image as a visible image.

During the scanning process, a portion of the storage radiation screen is illuminated with an excitation beam and emits light that is then collected by an image acquisition optics system. Generally, the excitation beam is directed toward the screen and scans across the screen line by line. The screen is induced by an excitation beam of a radiation source to luminesce pixel by pixel. Such scanning systems are described in U.S. Pat. Nos. 4,973,134, 4,543,479, 4,582,989, and 5,635,728. In particular, U.S. Pat. No. 5,635,728 describes a rotating scanner system to efficiently read multiple storage layer radiation screens. The carousel that holds multiple storage layer radiation screens is rotated about a rotational axis, and the screens adhered to the carousel are read by an image acquisition optical system positioned adjacent the carousel. As the carousel is rotated, the screen scanning system scans over a narrow line-shaped area of the screen perpendicular to the carousel's rotational axis. The movement of the optics module in the direction parallel to the rotational axis of the carousel enables the screen scanner to scan over different narrow line-shaped areas of the screens as the carousel is rotated, thereby enabling the entire surface area of the screen to be scanned.

It is important for screen scanning systems to produce images read from the screens which have minimal artifacts and distortions generated by the scanning system. For example, artifacts such as lines or bands seriously detract from the perceived quality of the images. A need thus exists for devices and methods which can improve the image quality produced by such scanning systems.

SUMMARY OF THE INVENTION

A system is provided for scanning an object, the system comprising: a drive shaft having a proximal portion and a longitudinal axis; a motor including a motor shaft having a rotational axis, the motor serving to rotate the motor shaft about the rotational axis; a flexible joint coupling the drive shaft to the motor shaft by the proximal portion of the drive shaft, the flexible joint having a range of motion which allows the longitudinal axis of the drive shaft to move relative to the rotational axis of the motor shaft; and an object attached to the drive shaft which is movable along the longitudinal axis of the drive shaft in response to the drive shaft being rotated by the motor.

A system is also provided for scanning an object adjacent a rotatable drum, the system comprising: a drive shaft having a proximal portion and a longitudinal axis; a motor including a motor shaft having a rotational axis, the motor serving to rotate the motor shaft about the rotational axis; a flexible joint coupling the drive shaft to the motor shaft by the proximal portion of the drive shaft, the flexible joint having a range of motion which allows the longitudinal axis of the drive shaft to move relative to the rotational axis of the motor shaft; an object attached to the drive shaft which is movable along the longitudinal axis of the drive shaft in response to the drive shaft being rotated by the motor; and a drum positioned adjacent the object, the drum being rotatable about a rotational axis that is approximately parallel to the rotational axis of the motor shaft.

A system is also provided for scanning storage layer radiation screens, the system comprising: a drive shaft having a proximal portion and a longitudinal axis; a motor including a motor shaft having a rotational axis, the motor serving to rotate the motor shaft about the rotational axis; a flexible joint coupling the drive shaft to the motor shaft by the proximal portion of the drive shaft, the flexible joint having a range of motion which allows the longitudinal axis of the drive shaft to move relative to the rotational axis of the motor shaft; an image acquisition optical system attached to the drive shaft which is movable along the longitudinal axis of the drive shaft in response to the drive shaft being rotated by the motor; and a drum positioned adjacent the image acquisition optical system, the drum being capable of holding one or more storage layer radiation screens and rotatable about a rotational axis that is approximately parallel to the rotational axis of the motor shaft.

In each of the above systems, the flexible joint preferably has a range of motion which allows the longitudinal axis of the drive shaft to move at least about 1 degree relative to the rotational axis of the motor shaft, optionally at least 5 degrees and optionally at least 10 degrees. Also in each of the above systems, the drive shaft preferably rotates at a substantially constant angular velocity during a revolution of the motor shaft despite drag of the drive shaft varying across a rotation of the drive shaft.

In each of the above systems, the flexible joint is preferably longitudinally stiff, i.e., the motion of the flexible joint is such that the drive shaft is not displaced longitudinally by the motion of the flexible joint. This longitudinal motion of an object attached to the drive shaft due to lateral motion of the drive shaft.

In one variation of the above systems, the flexible joint includes a first hub for attaching the motor shaft to the joint and a second hub for attaching the drive shaft to the flexible joint, the first and second hubs being movable relative to each other. The first hub preferably has a first range of angular motion within the flexible joint and the second hub has a second, different range of angular motion within the flexible joint. These first and second ranges of angular motion are preferably in planes orthogonal to each other.

In the design of the flexible joint used in the above systems, the flexible joint may optionally include a first hub for attaching the motor shaft to the joint and a second hub for attaching the drive shaft to the flexible joint, the first and second hubs each including hub pins by which the hubs are attached to the flexible joint and about which the hubs have a range of angular motion. According to this design, the hub pins are preferably held under compression within journals in the flexible joint.

BRIEF DESCRIPTION OF THE DRAWINGS

FIG. 6A shows a dental radiograph of a jaw generated by using a scanning system without a flexible drive assembly.

FIG. 6B shows a dental radiograph of a jaw generated by using a scanning system with a flexible drive assembly according to the present invention.

DESCRIPTION OF THE PREFERRED EMBODIMENTS

The present invention relates to a system for scanning an object where the system includes a flexible drive assembly which improves the scanning motion of the object.

In one embodiment, a system for scanning an object is provided which includes a drive shaft having a proximal portion and a longitudinal axis; a motor having a motor shaft for rotating the drive shaft about the longitudinal axis of the drive shaft; a flexible joint coupling the drive shaft to the motor shaft by the proximal portion of the drive shaft, the flexible joint having a range of motion which allows the longitudinal axis of the drive shaft to move relative to a rotational axis of the motor shaft; and an object attached to the drive shaft which moves along the longitudinal axis of the drive shaft in response to the drive shaft being rotated by the motor.

In another embodiment, a system is provided for scanning an object adjacent a rotatable drum, the system including a drive shaft having a proximal portion and a longitudinal axis; a motor having a motor shaft for rotating the drive shaft along the longitudinal axis of the drive shaft; a joint coupling the drive shaft to the motor shaft by the proximal portion of the drive shaft, the flexible joint having a range of motion which allows the longitudinal axis of the drive shaft to move relative to a rotational axis of the motor shaft; an object attached to the drive shaft which moves along the longitudinal axis of the drive shaft in response to the drive shaft being rotated by the motor; and a rotatable drum adjacent the object which rotates about a rotational axis that is parallel to the longitudinal axis of the drive shaft.

In another preferred embodiment, a scanning system for reading storage layer screens is provided which includes a drive shaft having a proximal portion and a longitudinal axis; a motor having a motor shaft for rotating the drive shaft along the longitudinal axis of the drive shaft; a flexible joint coupling the drive shaft to the motor shaft by the proximal portion of the drive shaft, the flexible joint having a range of motion which allows the longitudinal axis of the drive shaft to move relative to a rotational axis of the motor shaft; an image acquisition optical system attached to the drive shaft which moves along the longitudinal axis of the drive shaft in response to the drive shaft being rotated by the motor; and a rotatable drum capable of holding one or more storage layer screens adjacent the image acquisition optical system which rotates about a rotational axis that is parallel to the longitudinal axis of the drive shaft.

Figure 6C:
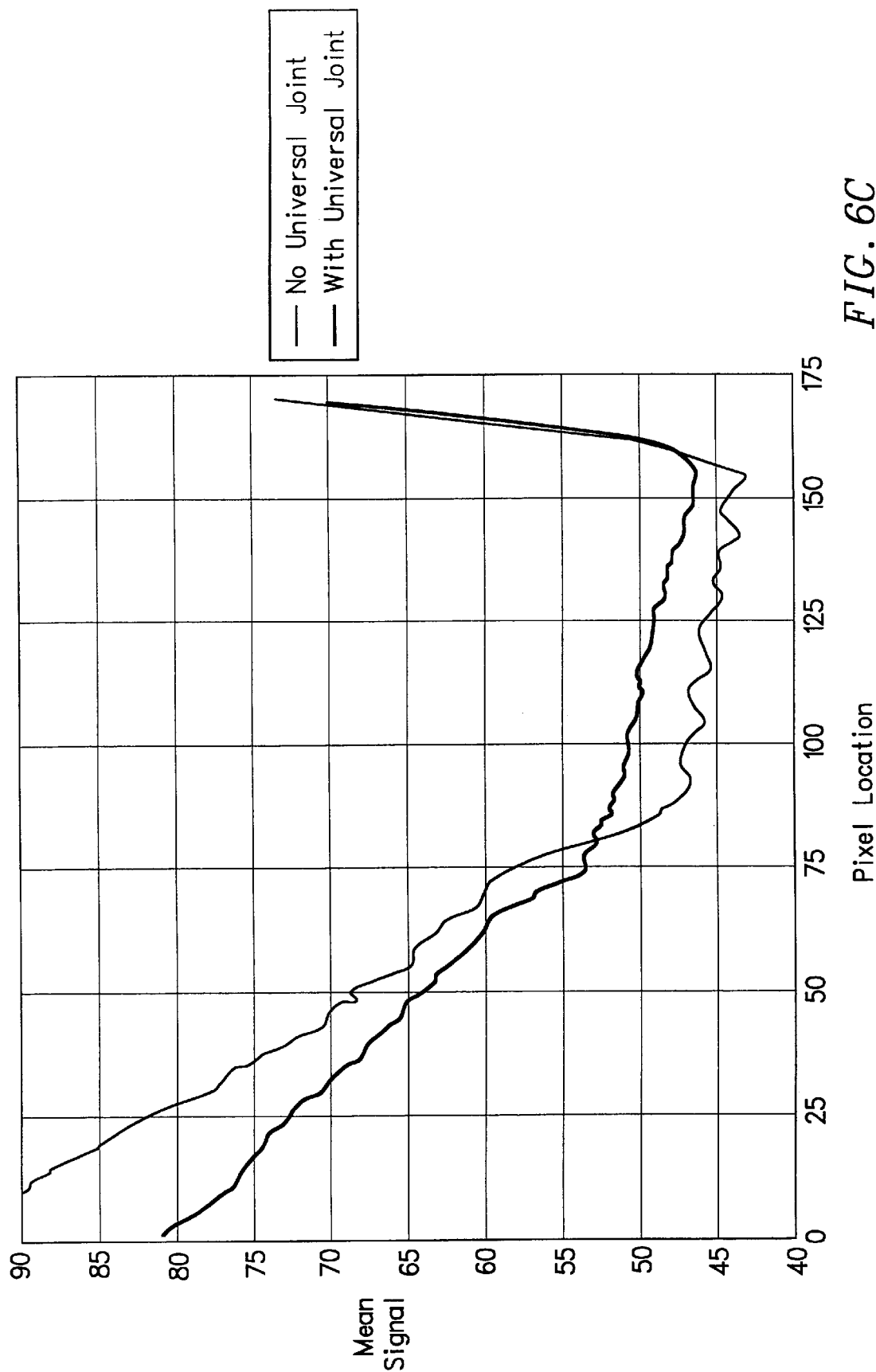
FIG. 6C shows linegraphs of the dental radiographs shown in FIGS. 6A and 6B. The linegraphs were generated by plotting the mean signals collected from the scanned screen relative to the pixel location of the screen. The light linegraph was generated by scanning the screen using a scanning system with a flexible drive assembly according the present invention; the dark linegraph by scanning the same screen using a scanning system without a flexible drive assembly.
Figure 6D:
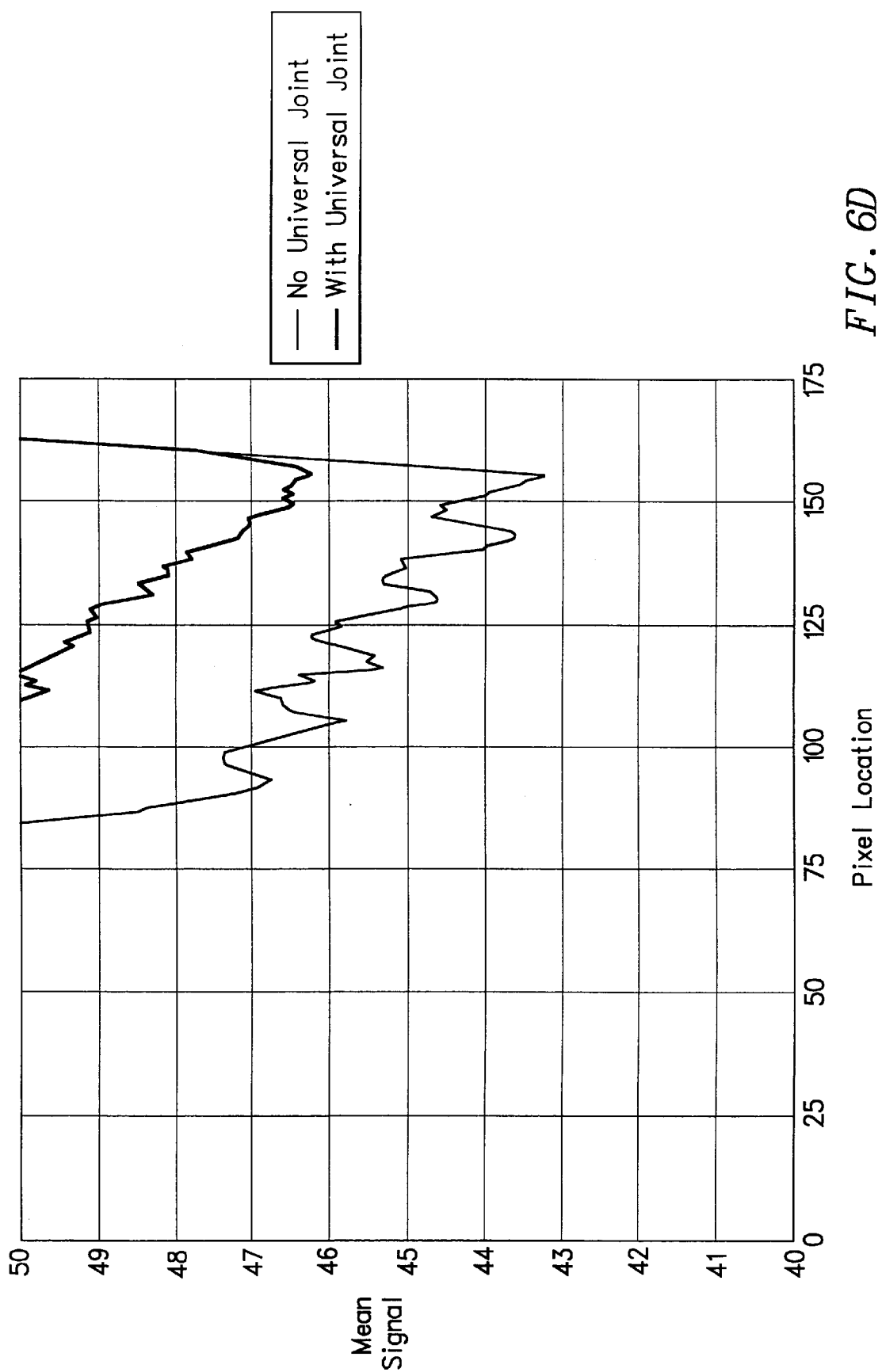
FIG. 6D shows a part of the linegraphs shown in FIG. 6C, and further demonstrates that mean signals acquired with the scanning system with the flexible drive assembly (light line) vary more linearly relative to the pixel location than the one acquired with the scanning system without a flexible drive assembly (dark line).

The present invention arises from the inventors' observation that banding appeared in a scanning system (DENOPTIX™ Digital Imaging System, Dentsply International, DesPlaines, Ill.), which is a drum scanning system without a flexible joint. FIG. 6A provides an example of an image taken with the scanner. By plotting a corresponding linegraph, shown in FIGS. 6C and 6D, it was observed that the banding occurs once per revolution of the drive screw system. Inventors modified the DENOPTIX™ Digital Imaging System to include a flexible drive assembly. As illustrated in FIGS. 6B and 6D, banding disappeared from the image (FIG. 6B) and from the linegraph (FIG. 6D) when a flexible drive assembly was used in the system.

Inventors believe that the flexible joint improves the quality of the image produced by a scanning system by improving the linearity of the scan rate of the system. More specifically, it is believed that small misalignments in the system cause a varying degree of drag to exist as the drive screw rotates. The varying degree of drag causes the rate at which the motor turns to fluctuate, which, in turn, causes banding to appear. By introducing a flexible drive assembly into the system, the drag in the system is believed to vary by a smaller degree, resulting in a more linear scan rate, and, hence, less banding.

One particular application for the present invention is its use in drum scanner systems for storage layer radiation screens. The process of scanning storage layer radiation screens is destructive in a way that, when stimulated by the laser, the phosphor on the screen releases energy in the form of light to be detected. In other words, the amount of energy that remains on the screen is decreased with each successive scan. If the distance between each scan line is shorter than the size of the spot (pixel) illuminated by the excitation laser beam on the screen, the part of the screen scanned by any given scan line will overlap scan lines before and after the scan line. If the velocity of the optics system is not constant, the amount of overlap between different scan lines will vary. This variation in amount of overlap results in varying amounts of energy reaching the image acquisition optics system, which, in turn, produces artifacts such as horizontal lines or bands in the image.

In the manufacture and/or assembly of the scanning systems, slight misalignments are difficult to avoid. Further, misalignments may occur during the course of operation and due to shocks (hits, droppings, etc.) to the system. These misalignments lead to fluctuations in the scan rate of the system, which causes the artifacts in the images. By using a flexible drive assembly in a scanning system according to the present invention, an object can be scanned at a more highly linear rate, thereby minimizing artifacts and/or distortions in the image.

Figure 1:
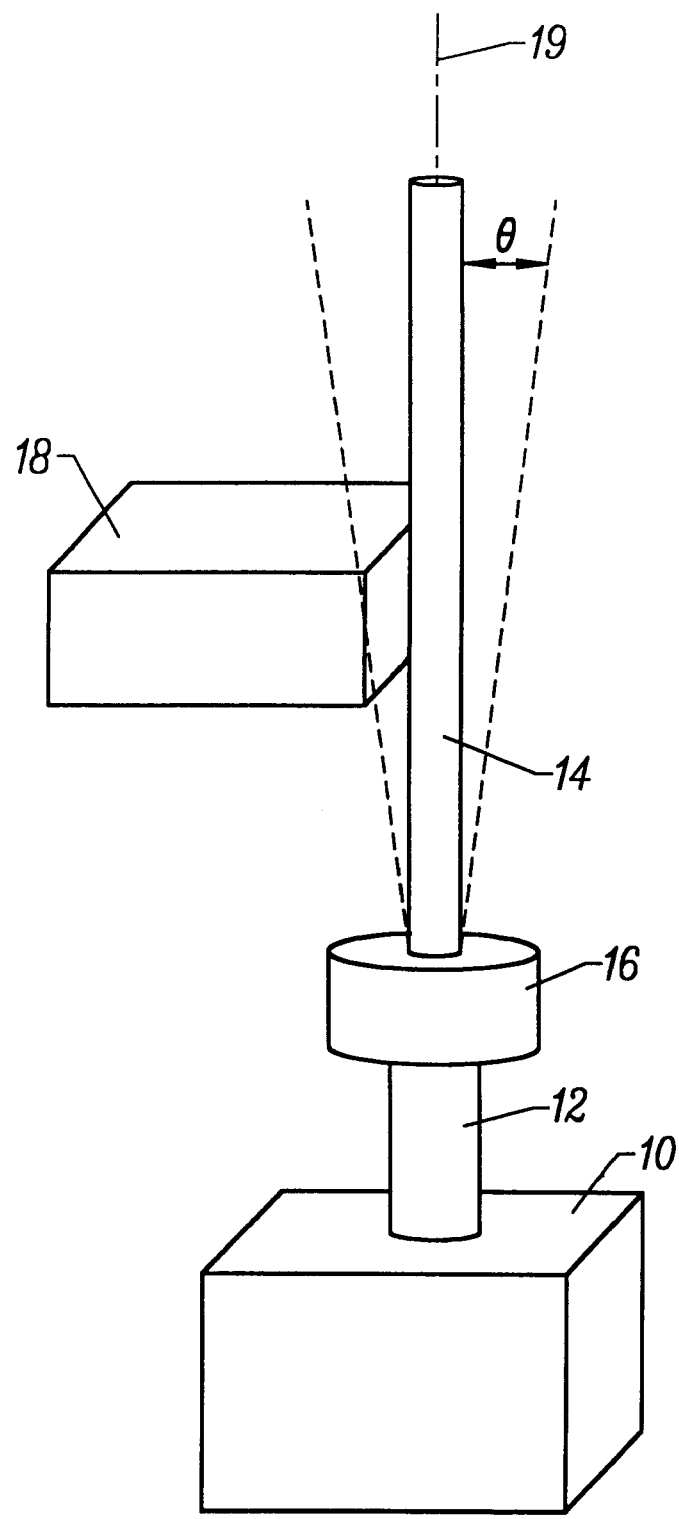
FIG. 1 illustrates a scanning system with a flexible drive assembly according to the present invention.

The flexible drive assembly used in the present invention includes a flexible joint for connecting a drive shaft to a motor shaft. The rotary driving force or torque exerted by the motor is transmitted through this linkage to the drive shaft. This flexible joint allows the longitudinal axis 19 of the drive shaft 14 to move relative to the rotational axis of the stationary motor shaft, preferably at least about 1°, more preferably at least about 5°, and most preferably at least about 10° (FIG. 1). Thus, addition of a flexible joint to the drive assembly results in a scanning system that is more tolerant to slight misalignments, thereby improving the quality of the image reproduced by the system.

An embodiment of a scanning system according to the present invention is illustrated in FIG. 1. As illustrated in FIG. 1, the scanning system includes a motor 10 having a motor shaft 12, a flexible joint 16, a drive shaft 14, and an object 18 to be scanned relative to drive shaft. A proximal portion of the drive shaft 14 is coupled to the motor 12 by the flexible joint 16. Meanwhile, the object 18 to be scanned is coupled to the drive shaft 14 and moves axially, as the drive shaft 14 is rotated. Rotation of the drive shaft 14 by the motor shaft 12 causes the object 18 to move along the drive shaft 14, thus translating the object 18 along the longitudinal axis of the drive shaft 14.

The flexible joint 16 has a range of motion which allows the proximal portion of the drive shaft 14 to move relative to the rotational axis of the stationary motor shaft 12, preferably at least about 1°, more preferably at least about 5°, and most preferably at least about 10°. This range of motion allows the scanning system to adjust itself in response to drag caused by slight misalignments in the system. As a result, the flexible joint 16 allows the motor shaft 14 to spin at a more constant rate which translates into a more linear scan of the object 18 by the system. When the motor shaft 12 rotates at a substantially constant angular velocity, the torque exerted by the stepper motor 12 is transmitted through the flexible joint 16 to the drive shaft 14, causing the drive shaft 14 to rotate at a substantially constant velocity. Consequently, the object 18 attached to the drive shaft can be moved along the longitudinal axis of the drive shaft 14 at a substantially constant velocity.

Figure 2:
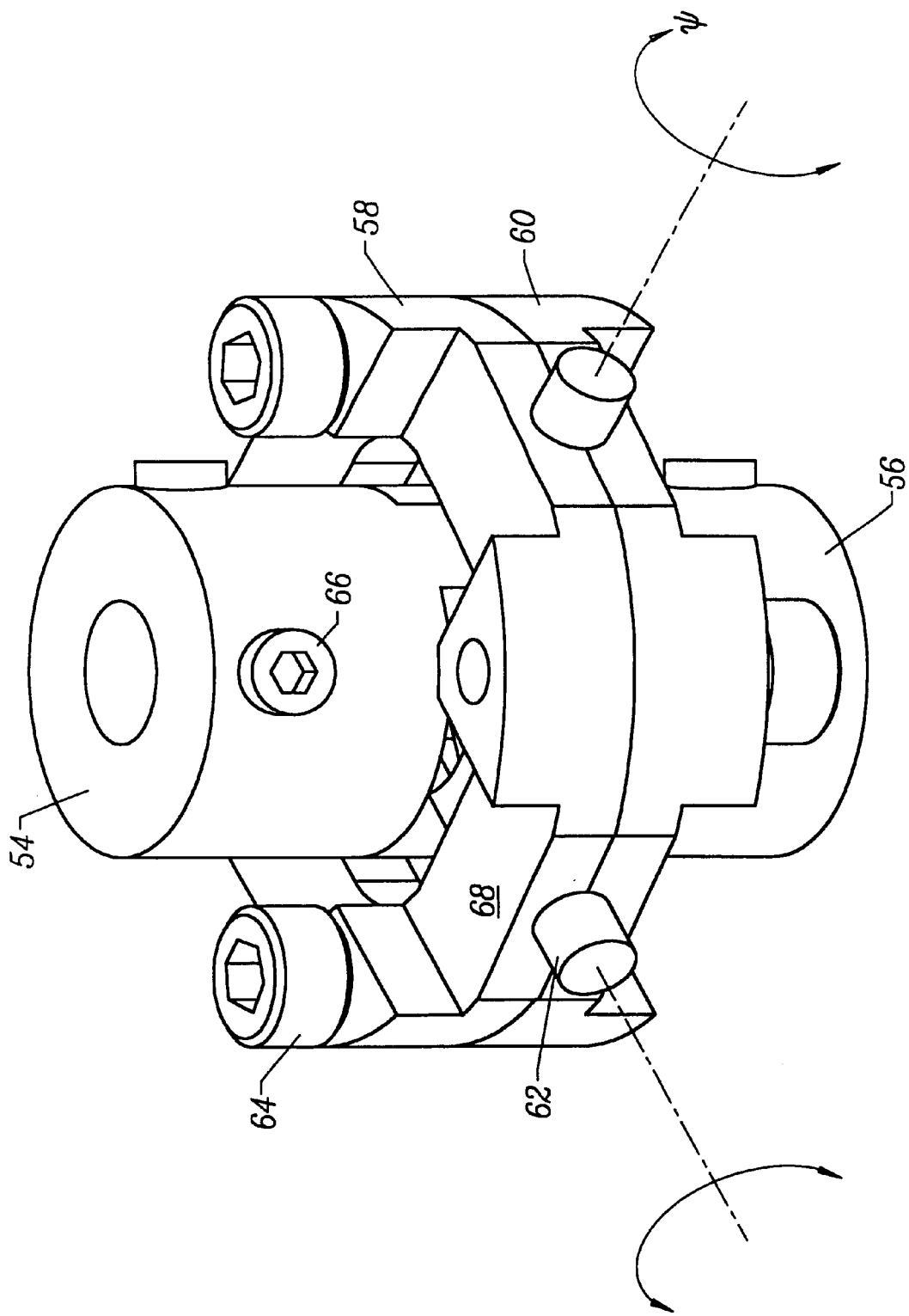
FIG. 2 illustrates an enlarged view of a flexible joint included in the flexible drive assembly of the scanning system shown in FIG. 1.

FIG. 2 provides an example of a flexible joint 16 that may be used with a scanning system of the present invention. As illustrated in FIG. 2, the joint consists of an upper hub 54 and a lower hub 56, each hub having transverse hub pins 62. The hubs are clamped together by an upper torque ring 58 and a lower torque ring 60 with clamping screws 64. Torque rings 58 and 60 form journals (holes) 70 which hub pins 62 can fit and rotate within about axis φ. This compressed assembly of the flexible joint 16 prevents backlash of the hub pins 62 within the journals, and also provides better durability for handling shocks to the scanner which may occur during shipping and handling.

Figure 3:
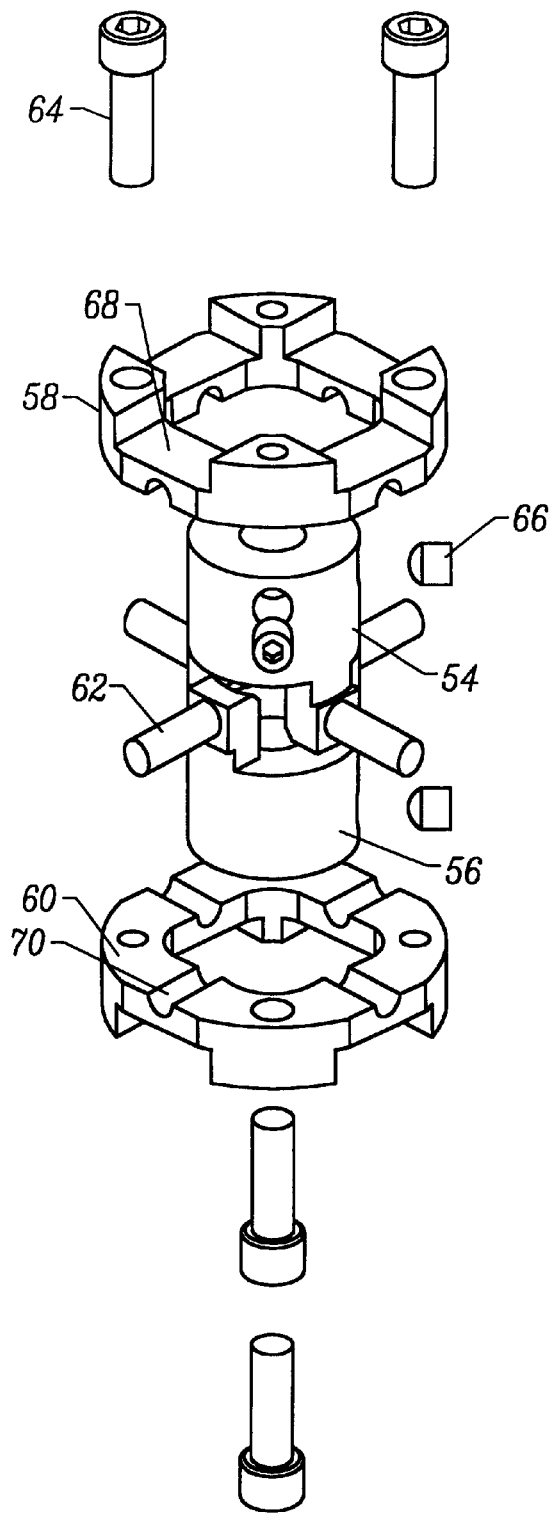
FIG. 3 illustrates the assembly of the flexible joint.

FIG. 3 provides a break-away illustration of the assembly of the flexible joint 16. As illustrated in FIG. 3, the upper hub 54 with two hub pins 62 is set onto the lower hub 56, also with two hub pins 62, forming a cruciform configuration. The upper torque ring 58 is mounted onto the upper hub 54, whereas the lower torque ring 60 is attached to the lower hub 56, in a manner that each hub pin is set on each journal 70 of the torque rings 58 and 60. The whole assembly is fastened by four clamping screws 64, with two of them clamping the upper torque ring 58 on the lower torque ring 60 and the other two clamping the lower torque ring 60 on the upper torque ring 58. Further, a proximal portion of the drive shaft 14 is mounted onto the upper hub 54 and fastened by two setscrews 66 through the upper hub 54. Further, the motor shaft 12 is fastened to the lower hub 56 by two set screws 66 through the lower hub 56.

The hub pins 62 roll within the journals 70 to allow the proximal end of the drive shaft 14 to move laterally relative to the longitudinal axis. The four notches 68 on each of the upper 58 and lower 60 rings are formed such that the notch is capable of flexing over the hubs 54 and 56, essentially creating a leaf spring.

The components of the flexible joint 16 may be made from a variety of durable materials. The upper 54 and lower 56 hubs are preferably made of brass. The upper 58 and lower 60 torque rings are preferably made of low friction plastic. A variety of materials, such as stainless steel or other alloy and Teflon or other polymer, may be used to manufacture the hubs and torque rings, respectively. A lubricating agent, such as oil or talc, may be applied to the joints to enhance smooth transmission of the rotary driving force exerted by the motor 10.

The flexible joint 16 can include a variety of mechanisms for joining the motor shaft 12 to the drive shaft 14. Examples include but not limited to Hook's coupling or a universal joint which may essentially consist of two fork members attached to the ends of the motor shaft 12 and the drive shaft 14, the fork ends being secured to a center cruciform member. Alternatively, another type of constant velocity joint may be used, consisting of a trunnion that contacts the inner circumferential surface of a holder, as described in U.S. Pat. No. 5,791,995.

The object 18 can be anything that is desirable to be attached to the drive shaft 14 of the scanning system. Examples include, but are not limited to, an object to be scanned and an image acquisition optics system.

Figure 4:
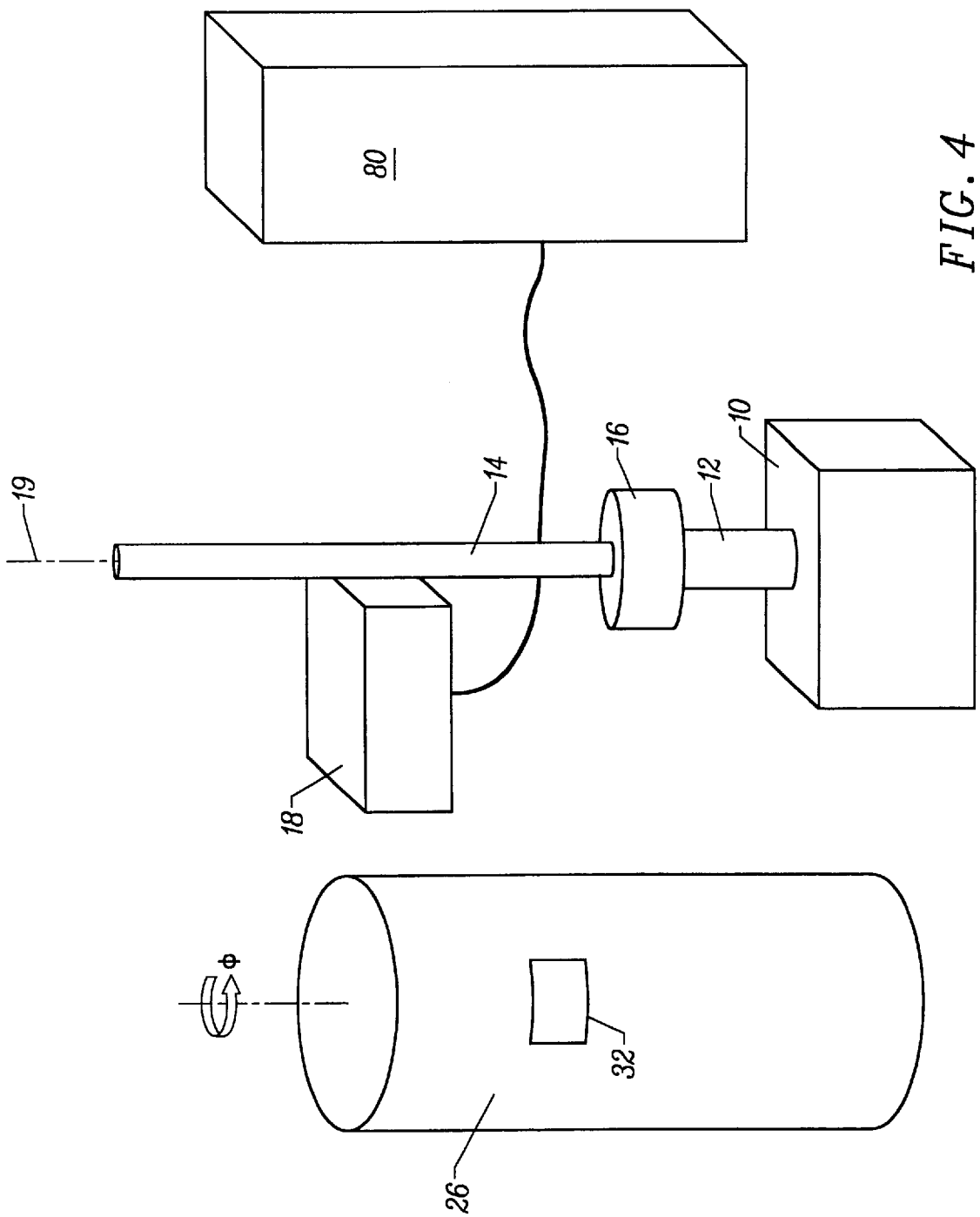
FIG. 4 provides an example of a screen scanning system with a drum and a data processing system.

In another embodiment, a system is provided for scanning an object adjacent a drum scanner. As illustrated in FIG. 4, the system includes a drive shaft 14 having a proximal portion and a longitudinal axis; a motor 10 having a motor shaft 12 for rotating the drive shaft along the longitudinal axis of the drive shaft; a flexible joint 16 coupling the drive shaft 14 to the motor shaft 12 by the proximal portion of the drive shaft, the flexible joint 16 having a range of motion which allows the longitudinal axis of the drive shaft 14 to move relative to a rotational axis of the motor shaft 12; an object 18 attached to the drive shaft 14 which moves along the longitudinal axis of the drive shaft 14 in response to the drive shaft 14 being rotated by the motor 10; and a rotatable drum 26 adjacent the object which rotates about a rotational axis φ that is parallel to the longitudinal axis of the drive shaft 14.

The rotatable drum 26 may be used to enhance the duty cycle of the scanning system by holding multiple images to be scanned. For example, the movement of an image acquisition optics system in the direction parallel to the rotational axis of the drum enables the image acquisition optics system to scan over different narrow line-shaped areas of the image, thereby enabling the entire surface area of the multiple images to be scanned. The drum may be designed to be removable from the scanning system, so that drums loaded with images scanned or to be scanned can be interchanged. By using a rotating drum, one can optionally adjust the rotation rate of the drum, the scanning speed of the scanning system as well as the sampling size of the scanning system while the scanning system is in operation. This enables the scanning system to be tuned and aligned in real time.

In another preferred embodiment, a scanning system for reading storage layer screens is provided. As illustrated in FIG. 4, the scanning system includes a drive shaft 14 having a proximal portion and a longitudinal axis; a motor 10 having a motor shaft 12 for rotating the drive shaft 14 along the longitudinal axis of the drive shaft 14; a flexible joint 16 coupling the drive shaft 14 to the motor shaft 12 by the proximal portion of the drive shaft 14, the flexible joint 16 having a range of motion which allows the longitudinal axis of the drive shaft 14 to move angularly; an image acquisition optical system 24 attached to the drive shaft 14 which moves along the longitudinal axis of the drive shaft 14 in response to the drive shaft 14 being rotated by the motor 10; and a rotatable drum 26 capable of holding one or more storage layer screens 32 adjacent the image acquisition optical system 24 which rotates about a rotational axis φ that is parallel to the longitudinal axis of the drive shaft 14. The scanning system may further include a data processing system 80 connected to the image acquisition optical system 24 for image outputs.

According to this embodiment of the present invention, the rotatable drum 26 may be used to hold one or more storage layer radiation screens 32 having the same size or different sizes. Preferably, the drum 26 may rotate about the rotational axis φ such that the screens 32 move in a circular path about the rotational axis φ. The maximum speed at which the drum 26 may be rotated is limited by the balancing of the drum. 35 Preferably, the drum 26 may be rotated at least about 60 revolutions per minute, more preferably at least about 300 revolutions per minute.

The rotation of the drive shaft 14, preferably between about 5–50 revolutions per minute, causes the image acquisition optics system 24 to move along the longitudinal axis of the drive shaft 14. It should be further noted that rotation of the drum 26 and movement of the image acquisition optics module 24 may be performed by different motors or by a single motor.

As the drum 26 is rotated about the rotational axis φ, the image acquisition optics system 24 scans the image stored on the screen 32 adhered to the rotatable drum 26. The image acquisition optics system 24 provides an excitation beam that is focused on a portion of the storage layer radiation screen 32 to cause light emission. As the screen 32 passes the image acquisition optics system 24, a different line-shaped portion of the screen 32 is read during each revolution of the drum 26, the width of the line corresponding to the width of a pixel. The image acquisition optics system 24 preferably reads pixels having a width between about 30 and 200 microns, more preferably between about 30 and 50 microns. As the drum 26 is rotated, the image acquisition optics module 24 is simultaneously moved in a direction parallel to the rotational axis φ of the drum 26 such that a new line-shaped portion of the screen 32 is read during each drum revolution. By moving the image acquisition optics system 24 at an appropriate speed, the image acquisition optics module 24 can scan over different narrow line-shaped areas of the screen 32, thereby enabling the entire surface area of the screen 32 to be scanned.

The light emitted from the screen 32 is then collected by the image acquisition optics system 24 and converted into an electrical signal. The electrical signal produced by the scanning system is communicated to a data processing system 80 which assembles the data collected and provides the user with one or more outputs corresponding to the image stored on the screen 32. For example, the data processing system can be connected to a data storage device (floppy disc, hard drive, floptical), an image reproducing device (monitor, printer), as well as a varity of communication devices (modem, network). The data processing system also enables the data collected to be manipulated by the user.

As shown in FIG. 6B, when a drum scanning system with a flexible joint according to the present invention is used, the image produced is substantially free of artifacts such as horizontal lines or bands, compared with the image produced by a drum scanning system without a flexible joint (FIG. 6A). The corresponding linegraphs, as shown in FIGS. 6C and 6D, are distinctly different, with the linegraph of the image (FIG. 6B) produced by the scanning system according to the present invention being much smoother and more linear.

Any storage layer screen can be used in conjunction with the scanning system according to the present invention. The storage screen may be formed of any compound which absorbs radiation, such as x-rays, $\alpha$-rays, $\beta$-rays, cathode rays and ultraviolet rays, and which, when stimulated by suitable electromagnetic wave radiation, emits electromagnetic wave radiation of a different frequency.

Figure 5:
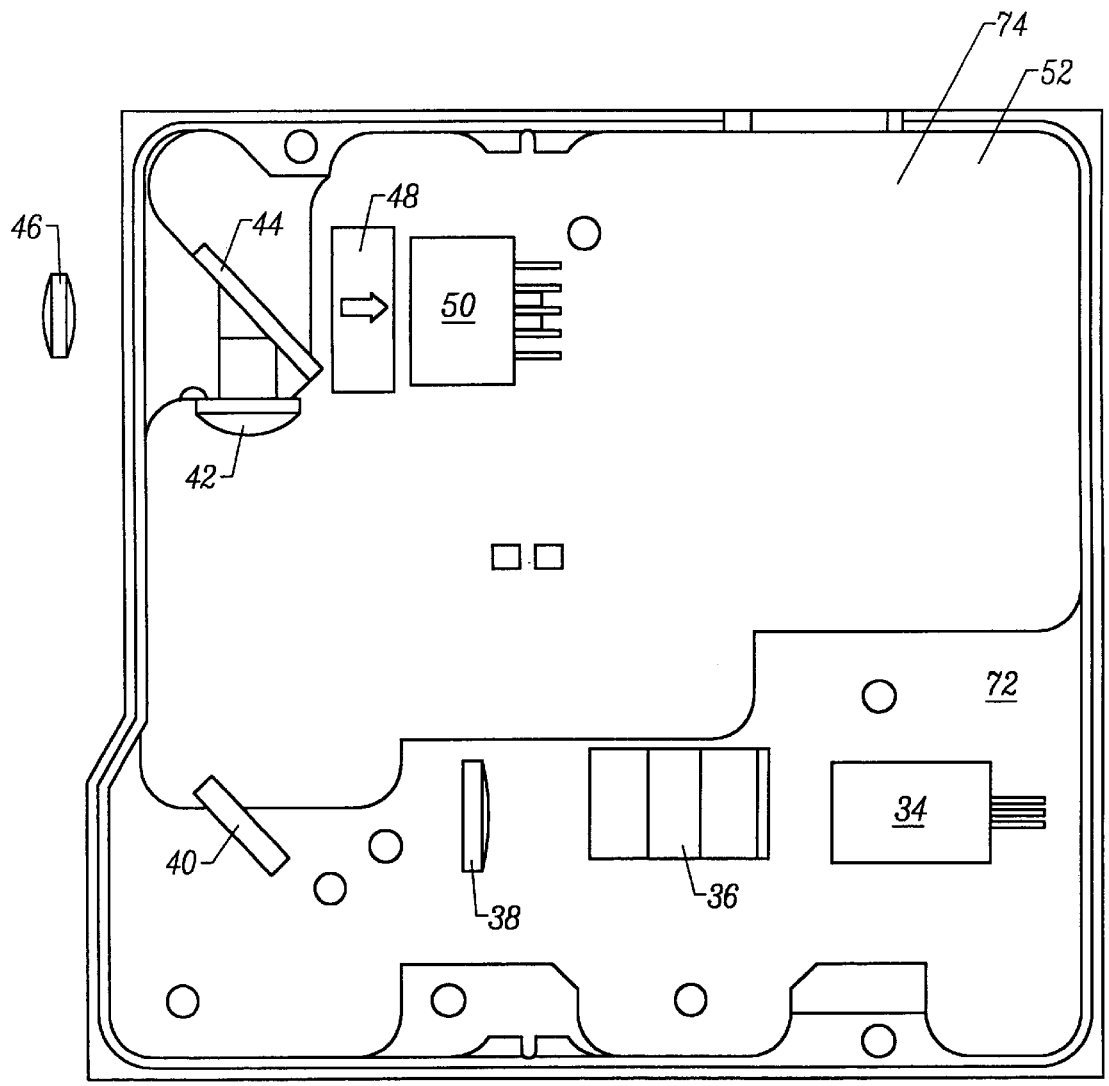
FIG. 5 illustrates an example of an image acquisition optics system that may be used in the scanning system.

An example of the image acquisition optics system 24 that may be used in the scanning system is illustrated in FIG. 5. The image acquisition optics system 24 includes an illumination system 72 and an emission collecting system 74 that is contained in an optics housing 52. The illumination system includes a laser 34 such as a HeNe or diode laser. The laser diode 34 produces an elliptical and astigmatic beam. The elliptical and astigmatic beam may optionally be corrected by anamorphic prism pairs 36 to produce a round excitation beam. A pair of cylindrical lenses can be used in place of the prisms 36. The diameter of the excitation beam may optionally be alterered using a telescope which consists of a first lens 38, a piano convex lens 38, a turning mirror 40, and a secondary lens 42. The turning mirror 40 reflects the excitation beam transmitted by the first lens 38 and transmits it to the second lens 42.

The excitation beam produced by the telescope is then reflected by a dichroic beam splitter 44 which reflects a high percentage of excitation beam, preferably at least 90%, more preferably at least 99%. The dichroic beam splitter 44 is preferably constructed of borosilicate glass with a dichroic coating.

The excitation beam reflected by the dichroic beam splitter 44 is focused by an objective lens 46 onto the screen 32. The objective lens 46 is preferably an aspherical lens which focuses the excitation beam onto a spot on a storage layer radiation screen, having a diameter of between about 30 and 200 microns, more preferably 35 and 50 microns, the diameter of the spot corresponding to the diameter of the pixel being read. The minimum size of the spot on which the excitation beam is focused is dependent on the amount of the rotatable 26 run out during rotation, a smaller amount of carousel run out enabling the excitation beam to be focused on a smaller spot on the screen.

An excitation beam of a frequency, e.g. 633 nm, focused on the screen causes the luminophores stored in the screen to emit light, an emitted light of a different wavelength, e.g., 390 nm or 400 nm, than that of the excitation beam. The wavelength of the emitted light is lower when a layer of a stimulatable phosphor is employed and higher when a layer of fluorescent material is employed. The intensity of the light emitted by the screen is proportional to the amount of radiation absorbed by the screen during exposure.

The light emitted from the screen 32 is collected by the emission collecting system 74 contained in the optics housing 52, also illustrated in FIG. 5. In addition to focusing the excitation beam on a spot on the screen 32, the objective lens 46 also serves to collect and collimate the light emitted from the screen 32. The focused emission light is then passed through the dichroic beam splitter 44 which transmits a high percentage of the light emitted by the screen 32, preferably at least 90%, more preferably at least 99%.

The emitted light transmitted by the dichroic beam splitter 44 is then passed through a color filter 48 that transmits the emission light while blocking most of the transmitted excitation light. The filter 48 serves to enhance the signal to noise ratio of the image acquisition optical system 24 by excluding light not corresponding to the light emitted from the sample, such as the transmitted excitation light.

Light transmitted through the filter 48 is then received by a photodetector 50 which converts the photos of energy received into electrical signals. The electrical signal produced by the photodetector 50 are then conveyed to a data processing system 80 for processing of the electrical signal. The electrical signals are subsequently processed to reproduce the latent radiation image as a visible image.

The photodetector 50 is preferably a photo multiplier tube (PMT) which is useful for optimizing low light level collection. Examples of other photodetectors that may be used in the image acquisition optics system 24 include a cooled metal silicon, avalanche photo diode, cooled CCD or CMOS or a pin diode. Alternate types of detectors may also be used in the image acquisition optics system 24 and are intended to fall within the scope of the present invention.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE

1. Comparison of Dental Radiographs taken by Scanners with and without Flexible Drive System The following example compares dental radiographs generated using a scanning system with and without the flexible drive system of the present invention.

Dental radiographs were obtained by using a storage layer radiation screen (6×12"; Pano Screen, Fuji) which was exposed using a GENDEX ORTHORALIX SD2 (74 kV, 10 mA, 12 seconds) using a standard panoramic settings. After x-ray radiation, the screen was scanned by a DENOPTIX™ Digital Imaging System (Dentsply International, DesPlaines, Ill.) which has a rigid drive assembly that directly couples the drive shaft to the motor shaft.

For comparison, the rigid drive assembly of the DENOPTIX™ Digital Imaging System was replaced by an embodiment of the present invention, a flexible drive assembly. The screen was scanned again under the same operating conditions by using the modified scanning system.

FIGS. 6A shows a dental radiograph of a patient's jaw acquired by using the DENOPTIX™ Digital Imaging System with the rigid drive system. In the image produced there are some horizontal lines or bands, more salient in the "darker" region corresponding to the area of lower mean signals/further pixel location in the linegraph shown in FIG. 6C.

In contrast, using the scanning system of the present invention to scan the same screen as described in FIG. 6A eliminated the "banding" problem. As shown in FIG. 6B, the dental radiograph is virtually free of artifacts such as horizontal lines or bands. Therefore, the quality of the image is significantly improved by using the scanning system with a flexible drive assembly according to the present invention.

FIG. 6C compares a linegraph of mean signals from an image acquired with the modified scanning system with the flexible drive system according to the present invention (light line), with the one acquired with DENOPTIX™ Digital Imaging System (dark line), relative to the pixel location of the image. As illustrated in FIG. 6C, the mean signals of the image acquired by the DENOPTIX™ Digital Imaging System with the rigid drive system vary in a sine wave fashion, shown more profoundly in the darker region where the intensity of the signal is lower. In contrast, the mean signals of the image acquired by the modified scanning system with the flexible drive system according the present invention follow a close-to-linear variation pattern.

To demonstrate the prominent effect of using the scanning system of the present invention on the quality of the signals acquired from the screen, FIG. 6D was generated by replotting a part of the linegraphs as shown in FIG. 6C. FIG. 6D shows that by using the scanning system of the present invention, the mean signals acquired vary much more linearly relative to the pixel location, whereas the mean signals acquired by using DENOPTIX™ Digital Imaging System with the rigid drive assembly vary in a sine wave fashion. It should be further noted that the frequency of this variation corresponds to each revolution of the drive shaft of the DENOPTIX™ Digital Imaging System with the rigid drive assembly.

What is claimed:

1. A system for scanning an object comprising:
   a drive shaft having a proximal portion and a longitudinal axis;
   a motor including a motor shaft having a rotational axis, the motor serving to rotate the motor shaft about the rotational axis;
   flexible joint coupling the drive shaft to the motor shaft by the proximal portion of the drive shaft, the flexible joint having a range of motion which allows the longitudinal axis of the drive shaft to move relative to the rotational axis of the motor shaft; and
   an object attached to the drive shaft which is movable along the longitudinal axis of the drive shaft in response to the drive shaft being rotated by the motor, wherein the drive shaft rotates at a substantially constant angular velocity during a revolution of the motor shaft despite drag of the drive shaft varying across a rotation of the drive shaft.

2. A system for scanning an object adjacent a rotatable drum comprising:
   a drive shaft having a proximal portion and a longitudinal axis;
   a motor including a motor shaft having a rotational axis, the motor serving to rotate the motor shaft about the rotational axis;
   a flexible joint coupling the drive shaft to the motor shaft by the proximal portion of the drive shaft, the flexible joint having a range of motion which allows the longitudinal axis of the drive shaft to move relative to the rotational axis of the motor shaft;
   an object attached to the drive shaft which is movable along the longitudinal axis of the drive shaft in response to the drive shaft being rotated by the motor; and a drum positioned adjacent the object, the drum being rotatable about a rotational axis that is approximately parallel to the rotational axis of the motor shaft, wherein the drive shaft rotates at a substantially constant angular velocity during a revolution of the motor shaft despite drag of the drive shaft varying across a rotation of the drive shaft.

3. A system for scanning or reading storage layer radiation screens comprising:

a drive shaft having a proximal portion and a longitudinal axis;

a motor including a motor shaft having a rotational axis, the motor serving to rotate the motor shaft about the rotational axis;

a flexible joint coupling the drive shaft to the motor shaft by the proximal portion of the drive shaft, the flexible joint having a range of motion which allows the longitudinal axis of the drive shaft to move relative to the rotational axis of the motor shaft;

an image acquisition optical system attached to the drive shaft which is movable along the longitudinal axis of the drive shaft in response to the drive shaft being rotated by the motor; and drum positioned adjacent the image acquisition optical system, the drum being capable of holding one or more storage layer radiation screens and rotatable about a rotational axis that is approximately parallel to the rotational axis of the motor shaft, wherein the drive shaft rotates at a substantially constant angular velocity during a revolution of the motor shaft despite drag of the drive shaft varying across a rotation of the drive shaft.

* * * * *